United States Patent [19]

Young et al.

[11] Patent Number: 4,654,442
[45] Date of Patent: * Mar. 31, 1987

[54] METHODS FOR REMOVING BIURET FROM UREA

[75] Inventors: Donald C. Young, Fullerton; James A. Green, II, Chino, both of Calif.

[73] Assignee: Union Oil Company of California, Los Angeles, Calif.

[ * ] Notice: The portion of the term of this patent subsequent to Feb. 24, 20004, has been disclaimed.

[21] Appl. No.: 567,047

[22] Filed: Dec. 30, 1983

[51] Int. Cl.⁴ ............................................. C07C 126/08
[52] U.S. Cl. ....................................................... 564/73
[58] Field of Search ........................................... 564/73

[56] References Cited

U.S. PATENT DOCUMENTS

| | | | |
|---|---|---|---|
| 3,150,177 | 9/1964 | Kluge | 564/38 |
| 3,184,508 | 5/1965 | Kaasenbrood | 564/73 |
| 3,846,298 | 11/1974 | Plura et al. | 521/26 |
| 3,903,158 | 9/1975 | Fuentes et al. | 564/73 |
| 4,345,099 | 8/1982 | Young et al. | 564/73 |

FOREIGN PATENT DOCUMENTS 146268 12/1978 Japan .

OTHER PUBLICATIONS

Kirk-Othmer, Encyclopedia of Chemical Technology, Third Edition, vol. 13, John Wiley and Sons, New York, pp. 678-705.
"Determination of Biuret in Urea by Ion Exchange Resins," *Soil and Plant Food*, vol. 3, No. 3, Jan. 1958, pp. 142-144, Takahashi and Yoshida.
"Determination of Biuret in Urea and Mixed Fertilizers", *Analytica Chemica Acta*, vol. 41, (1968), pp. 113-120, Geurts, Steele and Brinkman.
Mithyantha et al., Biuret and Crop Production, Fertilizer News, 1977.
Donald C. Young and James A. Green, II, application Ser. No. 567,271, filed Dec. 23, 1983, for Methods for Removing Biuret from Urea by Ion Exchange.
Donald C. Young and James A. Green, II, U.S. application Ser. No. 567,099, filed Dec. 30, 1983, for Ion Exchange Methods for Removing Biuret from Urea.
Redemann et al., *Ind. and Eng. Chem.*, vol. 50, No. 4, (1958), pp. 633-636.

*Primary Examiner*—Charles F. Warren
*Assistant Examiner*—C. S. Greason
*Attorney, Agent, or Firm*—Michael H. Laird; Gregory F. Wirzbicki; Dean Sandford

[57] ABSTRACT

Biuret is removed from biuret-containing aqueous urea solutions in a multi-cycle process which involves sequential (A) removal of biuret by contact with an anion exchanger and (B) regeneration of the anion exchanger, in which method, in one or more cycles, the anion exchanger regenerant comprises an aqueous solution of a strong base which has been employed to regenerate the anion exchanger in a previous cycle. This procedure allows for recycling, and thus reuse, of the strong base regenerant which results in significant economy. Methods are also provided in which (A) one or both of the aqueous urea solution and regenerant have a relatively low calcium equivalent content, (B) a substantially non-alkaline regenerant is employed either as the only regenerant in one or more cycles or as a partial regenerant before regeneration with the strong base regenerant, (C) the carbonate content of one or more of the aqueous process streams is controlled and/or reduced, and/or (D) the concentration of biuret in the recycled strong base regenerant is periodically reduced. All of these factors contribute to process economy, anion exchanger life, and more efficient, less frequent regeneration.

47 Claims, 1 Drawing Figure

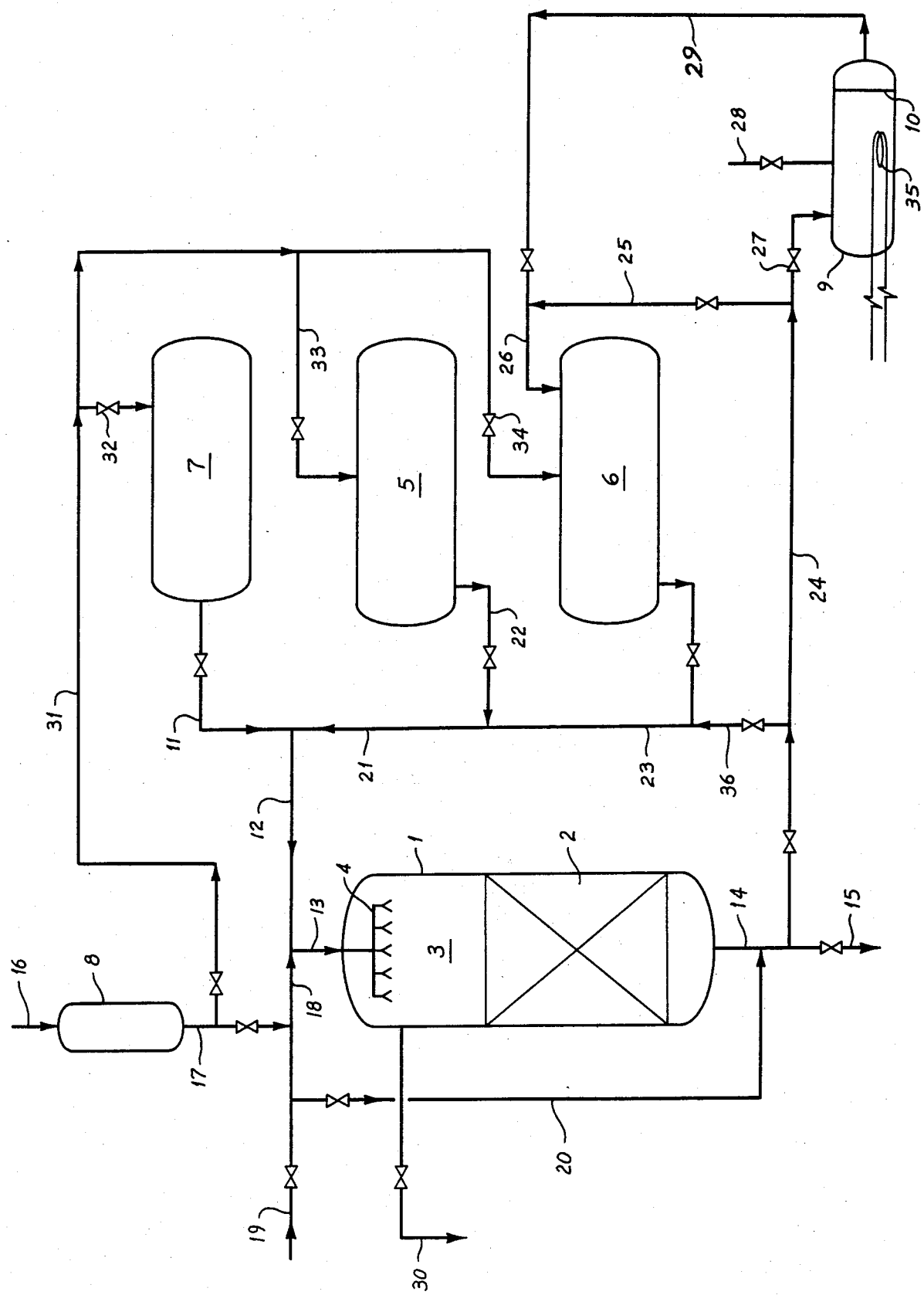

METHODS FOR REMOVING BIURET FROM UREA

BACKGROUND OF THE INVENTION

1. Field of the Invention

This invention relates to the field of urea purification, and in particular, it relates to methods for removing biuret from urea.

2. Description of the Art

Urea is a widely used fertilizer and chemical precursor. Most often it contains some biuret that forms during the urea manufacturing process or when urea is otherwise heated to 130° C. or above. Biuret can interfere with chemical processing and is toxic to many plants. Its phytotoxicity has been thoroughly studied, and it is regulated and monitored by government agencies and industry. For instance, the Indian government prohibits the import of urea containing more than 2 weight percent biuret. The United States agricultural industry generally observes an upper limit of 0.25 weight percent biuret for urea fertilizers classified as "low biuret." This criterion is generally recognized by the citrus and other industries that use urea for foliar fertilization.

Detectable biuret toxicity symptoms have been noted in field tests on lemon and grapefruit in Southern California at biuret levels as low as 0.1 weight percent. Biuret toxicity has also been observed with topically applied urea prills and solutions. Seed germination inhibition and damage to seedlings has been observed in wheat, barley and similar grain crops at levels of 2 weight percent biuret.

Damage to corn has been observed at foliar biuret dosages of 0.2 to 0.5 kilogram per hectare. Thirty percent yield loss was noted in one study at 1.7 kilograms biuret per hectare banded near seeds. Wheat damage has been observed at 0.2 to 0.5 kilogram per hectare foliarly applied, and severe toxicity was observed at 6.0 kilograms per hectare biuret banded in the soil. Fifteen to twenty ppm soil biuret level has been shown to inhibit barley seed germination while substantial crop damage from foliar application often occurs at 0.4 to 0.6 kilogram biuret per hectare.

Similar effects have been observed in rice, citrus, cotton, avocado, beans, soybeans and potatoes, several of which are particularly sensitive to biuret in foliar fertilizers. In citrus, as little as 0.2 kilogram foliarly applied biuret per hectare causes detectable damage. Avocados are damaged by as little as 50 ppm biuret in foliar sprays. As little as 3 kilograms per hectare biuret banded in the soil inhibits potato germination and causes citrus damage in light soils. These studies, and a comprehensive review of the literature available on this subject, are presented by Mithyantha, Kulkarni, Tripathi and Agnihothrudu, Fertilizer News, 1977, pp. 13–18.

In view of these results, it is not surprising that the industry has devoted substantial effort to methods of preventing biuret formation in the first instance, and to methods of reducing its concentration once it is formed. Most contemporary commercial urea plants are capable of producing solid and solution urea containing much less biuret than was previously the case. However, essentially all commercial ureas contain at least 0.5 weight percent biuret, and most contain from 1 to 2 weight percent biuret. Biuret content can rise considerably higher if manufacturing conditions are not adequately controlled.

One method for removing biuret from urea solutions is described by Fuentes et al. in U.S. Pat. No. 3,903,158, issued Sept. 2, 1975. Fuentes et al. describe a procedure in which a urea solution containing biuret is passed over either anionic or cationic exchange resins which, according to Fuentes et al., selectively retain biuret and allow urea to pass through the resin. The exchange resin can then be regenerated by contact with a basic solution after which the resin can be reused.

Another process for removing biuret from urea, disclosed by Young and Green in U.S. Pat. No. 4,345,099, involves treating a biuret-containing urea solution at a pH of about 12.5 or higher and a temperature of about 0° C. to about 100° C. under which conditions the biuret is hydrolyzed and thereby eliminated from the solution.

Takahashi and Yoshida, in "Determination of Biuret in Urea by Ion Exchange Resins", Soil and Plant Food, Volume 3, No. 3, January 1958, pages 142–144, disclose a process similar to that described by Fuentes et al., supra, in which biuret is removed from aqueous urea solutions by contact with a basic anion exchange resin. According to Takahashi et al., the biuret is quantitatively retained on the resin, even after water washing, thus allowing quantitative determination of biuret in aqueous urea solutions. The resin can be regenerated by acidic solutions, such as hydrochloric acid solutions, which contain chloride ion.

Another procedure for removing biuret from urea which is sufficiently quantitative to allow for its use as an analytical procedure, is disclosed by Geurts, Steele and Brinkman in "Determination of Biuret in Urea Mixed Fertilizers," Analytica Chimica Acta, Volume 41, (1968) at pages 113 through 120 Geurts et al. disclose that biuret which is first complexed with copper while in solution with urea, can be quantitatively removed from the solution by contact with certain ion exchange resins, and that the copper-biuret complex is not displaced from the resin by 0.9 molar ammonia or 0.3 molar sodium hydroxide solutions but can be eluted with 2 molar potassium nitrate followed by 0.2 molar nitric acid extraction.

General references to the characteristics and utility of anion exchangers such as strongly basic anion exchange resins are found in the trade literature such as Rohm & Haas Product Bulletin "Amberlite" IRA-400, Bulletin IE-16-56, revised April 1956, which discloses that Amberlite IRA-400 is a strongly basic anion exchange resin which can extract negative ions from either acidic, neutral or basic solutions. Biuret is known to be negatively charged in aqueous solutions. Thus, the Rohm & Haas bulletin suggests that strongly basic anion exchange resins such as Amberlite IRA-400 are capable of removing negatively charged ions such as biuret from either acidic, neutral or basic solutions.

Against this background, it can be seen that biuret can be effectively removed from aqueous urea solutions by the use of basic anion exchange resins, and that such methods require the use of relatively extensive anion exchanger and regeneration techniques.

Strongly basic anion exchangers such as Amberlite IRA-400 cost in the range of about $50 to about $150 per cubic foot. The strongly caustic or acidic solutions required to regenerate the exchangers are also relatively expensive. These regenerants must be sufficiently strong to dislodge the biuret from anion exchanger. Since, according to the literature, the biuret is relatively strongly held by the anion exchanger (a feature which would be beneficial from the standpoint of assuring adequate removal of biuret from the urea solution), the art suggests that relatively severe regeneration conditions are required to efficiently remove the biuret from the deactivated anion exchanger. Obviously, the cost of anion exchanger regeneration, the cost of constructing, maintaining and operating a system capable of removing biuret from a certain quantity of urea solution, and the expense of the anion exchanger required in the process, all increase as the frequency and/or severity of regeneration increases. Thus, the requirement for frequent and/or more severe regeneration increases the regenerant costs and the amount of anion exchanger and the size of the operating facility required to treat a given amount of urea solution.

We have now found that the frequency and severity of regeneration, the quantity of required anion exchanger, and the size of the operating plant required to remove biuret from aqueous urea solutions can be significantly reduced by employing novel biuret exchange and regeneration procedures in accordance with the methods of this invention.

It is therefore one object of this invention to provide improved methods for removing biuret from aqueous urea Another object is the provision of methods for removing biuret from urea solutions by ion exchange in which the cost of exchanger regeneration is reduced.

Yet another object is the provision of methods for removing biuret from urea solutions by ion exchange in which substantially non-alkaline aqueous media, such as water, can be employed as an exchanger regenerant thereby reducing regenerant expense.

Another object is the provision of methods for removing biuret from urea by ion exchange which increase the useful life of the anion exchanger.

Yet another object is the provision of methods for removing biuret from urea by ion exchange in which the frequency and duration of exchanger regeneration are reduced.

Yet another object of this invention is to reduce the cost of regenerant disposal associated with the removal of biuret from urea by ion exchange in which the ion exchanger is regenerated with basic regenerant.

Yet another object of this invention is to increase the rate of production of low biuret urea from biuretcontaining solutions.

Yet another object is the provision of methods for the removal of biuret from urea by ion exchange which reduce the exposure of the ion exchanger to deactivating components.

Other objects, aspects and advantages of this invention will be apparent to one skilled in the art in view of the following disclosure, the drawing, and the appended claims.

SUMMARY OF THE INVENTION

The methods of this invention involve a multi-cycle process which involves sequentially (A) contacting a basic anion exchanger with a biuret-containing urea feed solution to remove biuret from the solution and retain the biuret thus removed on the anion exchanger, and (B) removing retained biuret from the anion exchanger by contacting the exchanger with an aqueous regenerant, wherein, in at least one cycle, the aqueous regenerant comprises a biuret-containing aqueous solution of a strong base which has been previously recovered from the anion exchanger. Thus, the methods of this invention enable the use of the biuret-containing basic regenerant recovered from a previous cycle as the exchanger regenerant in one or more subsequent cycles. The methods of this invention optionally can involve the use of a substantially non-alkaline aqueous regenerant, such as water as the only regenerant employed in one or more cycles of the described multi-cycle process or as a preliminary regenerant which can be employed to remove a portion of the biuret from the deactivated exchanger before the exchanger is contacted with the basic regenerant.

Other embodiments of this invention provide for the removal of ion exchanger deactivating components from one or more of the various process streams including the aqueous urea feed solution and the regenerant solutions. Such deactivating components include hard water components such as calcium, magnesium, etc. (hereinafter referred to as calcium equivalents), carbonate anion, and/or compounds containing carbonate anions. Furthermore, in accordance with another optional embodiment of the methods of this invention, a portion or all of the biuret contained in the basic regenerant recovered from regeneration of the anion exchanger can be converted to materials which do not diminish the exchange efficiency of the anion exchanger (such as urea and ammonia) and which can be recovered as useful items of commerce such as fertilizers.

BRIEF DESCRIPTION OF THE DRAWING

The invention will be more readily understood by reference to the drawing which is a schematic illustration of a cyclical ion exchange system which can be employed in accordance with one embodiment of this invention.

DETAILED DESCRIPTION OF THE INVENTION

This invention provides methods for removing biuret from urea in a multi-cycle process in which, in each cycle, (A) biuret is removed from a biuret-containing aqueous urea feed solution by contacting the feed solution with a basic anion exchanger, and (B) the anion exchanger containing retained biuret is regenerated by contact with an aqueous regenerant, wherein, in one or more cycles, the aqueous regenerant comprises an aqueous solution of a strong base which has been previously recovered from the anion exchanger regeneration step. Thus, the aqueous regenerant containing a strong base which has been employed to regenerate the anion exchanger in a previous cycle can be employed to regenerate the anion exchanger in one or more subsequent cycles even when regenerant contains biuret extracted from the anion exchanger in one or more previous cycles. Optionally, a substantially non-alkaline aqueous medium, such as water, can be employed as the sole regenerant in one or more cycles, or as a partial regenerant before the ion exchanger is further regenerated with the strong base regenerant.

The methods of this invention also optionally provide for the removal of anion exchanger deactivating components such as carbonate and "hard" water components from the biuret-containing urea feed and/or the alkaline or non-alkaline regenerants to prevent contamination and deactivation of the anion exchanger by such components.

Further economy can be achieved in accordance with another optional embodiment of this invention which provides for the removal of biuret from the recycled basic regenerant which procedure thereby reduces or eliminates interference of biuret contained in the regenerant with regeneration efficiency.

The methods of this invention reduce or eliminate the expense and inefficiencies associated with several aspects of processes which are otherwise available for removing biuret from urea. For instance, the methods of this invention reduce the expense of the strong base regenerant employed to regenerate the anion exchanger, in part, by providing for the recycle of aqueous solution of a strong base recovered from a previous regeneration step and by reducing the concentration of exchanger deactivating components in the recycled strong base regenerant. The cost of strong base regenerant is also reduced by employing water as a partial regenerant or as a sole regenerant in at least some cycles of the methods of this invention.

The useful life and efficiency of the anion exchanger are both increased, in accordance with the methods of this invention, in part, by eliminating exchanger-deactivating components from the urea feed and/or aqueous regenerant. Increased exchanger efficiency increases the amount of biuret that can be removed from the urea feed solution in each cycle and reduces regeneration cost. Increased exchanger useful life results in obvious economy and further reduces process down time which would otherwise be required to recharge the system with fresh anion exchanger.

All of these aspects result in higher overall production rates of low or zero biuret urea and reduce the overall process expense required to produce a given quantity of low biuret urea product. Further economies result from reduced caustic regenerant disposal expense since much less caustic is discharged in the methods of this invention than is the case in alternative processes such as those disclosed by Fuentes et al.

The biuret-containing, aqueous urea feed solutions which can be treated in accordance with the methods of this invention include all such solutions which are either manufactured or employed in any industry. Most of these solutions contain at least about 0.5 weight percent, generally about 1 to about 90 weight percent and most commonly about 1 to about 70 weight percent urea. Greater economy is realized in these methods by employing relatively concentrated urea solutions in order to reduce the volume of material handled and reduce the exposure of the anion exchanger to impurities contained in the urea feed solution. Thus, preferred urea solutions usually contain about 10 to about 70 weight percent urea.

The biuret concentration in the urea feed can vary considerably but will usually be at least about 0.1 weight percent biuret based on urea. Most commercial ureas, however, contain at least about 0.5 weight percent, generally about 0.1 to about 10 weight percent, and most commonly about 0.1 to about 5 weight percent biuret based on urea.

The anion exchangers which are useful in the methods of this invention can be either organic or inorganic, basic ion exchangers or combinations of organic and inorganic anion exchangers. The anion exchanger is preferably at least moderately basic and is most preferably a strongly basic anion exchanger such as the anion exchangers marketed by Rohm & Haas Company under the trademark Amberlite ® IRA-400, IRA-458, and IRA-900, and the like, anion exchangers marketed by the Dow Chemical Company under the trademark Dowex I-X4, anion exchangers marketed by the BI-ORad Company under the trademark AG MP-1, and others.

The presently preferred anion exchangers are the strongly basic, organic ion exchange resins which contain tertiary and/or quaternary amine groups. Such anion exchangers can be prepared by the chloromethylation of a styrene-divinylbenzene copolymer which is then reacted with a tertiary or secondary amine; by the condensation of phenylenediamine with formaldehyde; or by the condensation of phenylenediamine, polyethyleneimine and formaldehyde. Particularly preferred anion exchangers are the quaternary amine types such as those disclosed in U.S. Pat. No. 2,591,573, the disclosure of which is incorporated herein by reference.

The hydroxide ion form of the anion exchangers is presently preferred to effect the removal of biuret from the biuret-containing urea solutions in accordance with the methods of this invention. However, many of the commercially available anion exchangers are manufactured and sold in other ionic forms, such as the chloride form, and require conversion to the hydroxide ion form prior to use in the methods of this invention. Conversion of the anion exchanger to the preferred hydroxide ion form can be readily accomplished by contacting the anion exchanger with an aqueous solution of a strong base as described, for instance, in "Ion Exchange with the Amberlite Resins" and "Amberlite IRA-400 - Laboratory Manual", both of which are available from the Resinous Products Division, Rohm & Haas Company, Washington Square, Philadelphia, 5, Pennsylvania, and both of which are incorporated herein by reference.

The aqueous solutions of strong base useful in the methods of this invention are employed to convert the non-hydroxide forms of anion exchangers, e.g., the chloride form, to the preferred hydroxide form and to regenerate the biuret-containing anion exchanger after the exchanger has been employed to remove biuret from the urea feed solution. The strong bases useful in these methods include both organic and inorganic bases and should be capable of producing a pH in water of at least about 11.5, preferably at least about 13, and most preferably about 14. Illustrative organic and inorganic bases include tetramethylammonium hydroxide, triethylamine, ammonium hydroxide, and the alkali metal hydroxides and their water soluble precursors such as lithium, sodium, potassium, cesium and rubidium hydroxides and hydroxide precursors. The alkali metal hydroxides, particularly sodium and potassium hydroxides and hydroxide precursors, are presently preferred. Although ammonium hydroxide is a useful basic regenerant in concentrations up to about 10 weight percent ammonia, surprisingly, it interferes with rather than benefits regeneration, particularly with the preferred organic anion exchanger resins, at substantially higher ammonia concentrations, e.g., 25 weight percent ammonia.

The concentration of base in the strong base solutions useful in the methods of this invention will usually be at least about 0.5 weight percent, normally about 0.5 to about 25 weight percent, preferably about 1 to about 10 weight percent and most preferably about 2 to about 6 weight percent. The base concentration should be sufficient to convert the anion exchanger to the desired hydroxide ion form and/or to displace biuret retained on the anion exchanger after the anion exchanger has been employed to remove biuret from the urea feed solution.

Chloride ion-containing solutions can be employed in accordance with the methods of this invention to regenerate the deactivated anion exchanger when more severe regeneration is desired than can be obtained readily with the substantially non-alkaline and/or strong base regenerant. For instance, it is sometimes useful to employ chloride ion-containing solutions to remove excessive accumulations of carbonate and/or alkaline earth compound deposits and/or other impurities which accumulate on or in the anion exchanger. The chloride ion-containing solutions useful for this purpose are aqueous solutions of ionizable organic or inorganic chloride-containing compounds such as the alkali metal chlorides which usually contain at least about 0.5, preferably at least about 1, and generally about 1 to about 10 weight percent of the chloride-containing compound. Sodium and potassium chlorides are presently preferred.

Acidic chloride ion-containing solutions more rapidly and effectively regenerate the anion exchangers than do non-acidified solutions. Preferred acidified solutions normally have pH levels of about 3 or less. Relatively dilute hydrochloric acid solutions and sodium chloride solutions which have been acidified with an acid, such as hydrochloric acid, are presently preferred. Hydrochloric acid, when employed, will usually be present in the chloride solution at a concentration of at least about 0.001 normal, preferably at least about 0.01 normal and generally about 0.1 to about 3 normal.

Water is conventionally employed to backwash the ion exchange resin to remove accumulated debris, to expand and reclassify the bed of anion exchanger particles, and/or to remove residual process fluids such as the process feed or regenerant, either prior to regeneration or prior to reuse following regeneration. However, we have found that water and other non-alkaline aqueous media can also be employed to remove a significant proportion of the biuret retained on the anion exchanger after its use. The discovery that anion exchangers which efficiently remove biuret from aqueous solutions can be regenerated by a non-alkaline aqueous medium such as pure water was surprising, and its use as an optional regenerant can result in substantial economies in the methods of this invention. Water or other non-alkaline aqueous media can be employed either as a partial regenerant prior to further regeneration with the aqueous solution of a strong base, or it can be used as the only regenerant in one or more cycles of the multicycle process. Such use of non-alkaline regenerants markedly reduces the amount of strong base which is required to maintain anion exchanger activity The substantially non-alkaline aqueous media which can be employed as regenerants in the methods of this invention will have pH levels below about 11.5, preferably below about 10, most preferably below about 8, and will usually contain less than about 0.1 weight percent of a strong base. The term "substantially non-alkaline" is employed herein to distinguish aqueous regenerants and wash media which have pH levels below 11.5 from the more strongly alkaline regenerants which are aqueous solutions of a strong base and which have pH levels of 11.5 or above. The substantially non-alkaline aqueous media can contain other components which are not strongly basic and which do not diminish the ability of the non-alkaline aqueous media to remove biuret from the anion exchanger. Thus, the substantially non-alkaline aqueous media can contain minor amounts of weak base, chloride ion, and/or other components.

At least one of the aqueous process streams can be treated to reduce its calcium equivalent (alkaline earth metal) content and/or carbonate content, and/or can be prepared from water of low calcium equivalent and/or carbonate content or from water which has been treated to reduce its calcium equivalent and/or carbonate content. Preferably, the calcium equivalent and/or carbonate contents of all of the aqueous process streams employed in these methods are controlled by such procedures. We have also found that the activity and efficiency of the anion exchangers can be markedly diminished by contaminants present in the urea feed solution, the water from which all of the aqueous solutions employed in the process are derived, and which are generated in the process itself, particularly in the strong base recycle system. Principal among these contaminants are alkaline earth metal compounds and carbonate ion. Carbonate ion (including carbonate compounds) is usually present in commercially available urea solids (prills, granules, etc.) and urea solutions, and may be present in the water employed in any one of the aqueous streams employed in the methods of this invention. We have also found that carbonate ion is generated in the aqueous solution of a strong base following its use to remove biuret from the anion exchanger. The so-called "hard" water components, principally calcium and magnesium ions, also contribute to anion exchanger deactivation and inefficiency. The greater portion, if not all, of these hard water components enter the system in the water employed to produce one or more of the aqueous process streams.

As a result of these findings, we have discovered that the activity, efficiency, and lifetime of the anion exchanger can be markedly improved, and that the amount of strong base, non-alkaline, and chloride ion regenerants required to maintain anion exchanger activity and efficiency can be markedly reduced, by employing aqueous process streams which have relatively low concentrations of carbonate and/or "hard" water contaminants.

It is presently preferred that the "hardness" of the water employed in one or more of the aqueous process streams in the methods of this invention corresponds to less than 1, preferably less than 0.5, and most preferably less than about 0.2 calcium milliequivalents per liter. These limits correspond approximately to less than about 20 parts per million, preferably less than 10 parts per million, and most preferably less than about 4 parts per million equivalent calcium ion. Preferably, the aqueous solutions themselves, including the biuret-containing urea feed, the aqueous solution of a strong base, the non-alkaline regenerant, wash media, and other aqueous process fluids, also meet this criteria.

The terms "equivalent calcium" and "calcium milliequivalents per liter" are conventionally used in the art to refer to the degree of water "hardness" and include water hardness that is attributable primarily to alkaline earth metals, especially calcium and magnesium. The value for calcium milliequivalents per liter can be determined by complexmometric-colorometric titration with ethylenediamine tetraacetic acid (EDTA) as discussed by Homer D. Chapman and P. F. Pratt in "Methods of Analysis for Soils, Plants and Waters," University of California, Division of Agricultural Sciences, 1961. The approximate concentration of equivalent calcium (which includes calcium and other alkaline earths) in parts per million can be determined by multiplying the value for calcium milliequivalents per liter by 20.

Calcium equivalent content can be reduced and/or controlled by the use of naturally occurring soft waters such as some mountain streams and rivers and by the use of distilled and ion exchanged water sources. Suitable exchanged waters include water which have been decationized (hydrogen exchanged), deionized, sodium exchanged ("soft"), and water sources which have been exchanged with cations which do not form water insoluble carbonates.

The carbonate content (including bicarbonate which is often referred to as "temporary hardness") of the water employed to form the aqueous process streams useful in these methods, as well as the carbonate content of the process streams themselves, is advantageously maintained at a level of about 35 parts per million or less, preferably about 20 parts per million or less, and most preferably within the range of 0 to 10 parts per million by weight.

Carbonate content can be controlled by the use of naturally occurring low carbonate waters such as mountain streams and rivers, and by the use of distilled or ion exchanged water sources or combinations of such sources. Suitable ion exchanged low carbonate water sources include waters in which the carbonate anion has been replaced by one or more anions which minimize competition with biuret for exchange sites. Various ions are suitable for this purpose with hydroxide ion being most preferred and nitrate, sulfate, and chloride ions being less preferred. The carbonate content of water supplies which are unacceptably high in carbonate content also can be controlled by removal of carbonate contaminant by any one of several known procedures such as by precipitation of the carbonate as insoluble alkaline earth metal carbonate. Such carbonate precipitation can be achieved by adding to the water supply an amount of an organic or inorganic alkaline earth metal compound and separating the precipitated alkaline earth carbonate by filtration, decanting, or other method of liquid-solid separation. Calcium and magnesium compounds, and combinations of such compounds, are presently preferred. Illustrative alkaline earth metal compounds are the calcium and magnesium hydroxides, chlorides, sulfates, nitrates, hydrogen phosphates, acetates, and the like, with the hydroxides being particularly preferred.

The alkaline earth metal compound is preferably added only in the amount necessary to react with and precipitate the carbonate contained in the water supply or process stream. Thus, the amount of added alkaline earth metal compound preferably does not exceed the stoichiometric amount required to react with carbonate. Most preferably, the alkaline earth metal compound is added in an amount corresponding to about 90 percent or less of the stoichiometric amount of alkaline earth metal required to react with the carbonate in order to reduce the possibility of contaminating the anion exchanger with alkaline earth metals.

The described water and process stream selection and/or treatment procedures are usually sufficient to reduce the concentration of alkaline earth metals and/or carbonate to acceptable levels. For instance, sodium exchange can reduce equivalent calcium content to less than 1 part per million (less than 0.05 calcium milliequivalents per liter), and deionization can be employed to reduce calcium content to levels of about 0.5 parts per million (0.025 calcium milliequivalents per liter).

In accordance with the methods of this invention, at least a portion of the biuret contained in a biuret-containing aqueous urea solution is removed by contacting the urea solution with the hydroxide ion form of an anion exchanger useful in the methods of this invention under conditions sufficient to remove at least a portion of the biuret from the urea solution and retain the thus removed biuret on the anion exchanger. The urea solution of reduced biuret content is recovered from the anion exchanger, and the anion exchanger is contacted with fresh quantities of the biuret-containing urea solution until either the desired quantity of reduced biuret urea product has been obtained or the capacity of the anion exchanger for removing biuret from the urea solution has diminished to a point that regeneration is required. At that point, the ion exchanger can be regenerated in accordance with this invention by contacting the anion exchanger with an aqueous regenerant under conditions which are sufficient to remove at least a portion of the biuret retained on the anion exchanger and restore at least a portion of the activity of the anion exchanger for removing biuret from additional quantities of the biuret-containing urea solution. The thus formed biuret-containing regenerant is then recovered from the anion exchanger and the cycle is repeated as desired to remove biuret from fresh quantities of the biuret-containing urea solution.

The methods of this invention can be employed to reduce the biuret content of the biuret-containing urea solutions to essentially any desired level depending on the treatment conditions chosen. Normally, however, the process conditions will be selected to produce a product urea solution having a biuret content of about 0.5 weight percent or less, often of about 0.2 weight percent or less, and, if desired, of about 0.1 weight percent or less. In fact, the methods of this invention can be employed to reduce the biuret content of any selected biuret-containing aqueous urea solution to undetectable levels.

A salient aspect of the methods of this invention is that the aqueous regenerant employed in at least one cycle of the process is an aqueous solution of a strong base which has been recovered from the anion exchanger in a previous regeneration step. In each cycle of the process, the aqueous regenerant employed to remove biuret from the biuret-containing anion exchanger can be either the aqueous solution of a strong base, a substantially non-alkaline aqueous regenerant, or combinations of the two. When combinations of strong base solutions and non-alkaline aqueous regenerants are employed, the biuret-containing anion exchanger is preferably contacted first with the substantially non-alkaline regenerant to remove at least a portion of the biuret from the anion exchanger and is then contacted with the aqueous solution of a strong base to remove further portions of the biuret from the anion exchanger.

Thus, the methods of this invention enable the reuse of the strong base regenerant which results in substantial economy in the overall process. The aqueous solution of a strong base can be reused for at least one cycle, usually at least two cycles, preferably for at least four cycles, and generally for about four to about twenty cycles before it is discharged from the system. We have found that it is generally desirable to recycle the aqueous solution of a strong base until the base has been approximately half consumed by regeneration of the anion exchanger.

The number of cycles in which an aqueous solution of a strong base can be employed depends on the initial quantity or inventory of strong base solution relative to the quantity of biuret to be removed, the initial concentration of strong base in the basic regenerant solution, the amount of biuret that is retained on the anion exchanger in each cycle, and the presence of impurities in the system such as alkaline earth metal ions and carbonate ion. For instance, one gallon of strong base regenerant having an initial sodium hydroxide concentration of about 4 weight percent will be approximately half depleted in regenerating one gallon of an anion exchanger which has been employed to remove 0.5 weight percent biuret from 9 gallons of an aqueous urea solution. One gallon of basic regenerant having an initial sodium hydroxide concentration of 6 weight percent could be employed to regenerate more than one gallon of the same anion exchanger under otherwise identical conditions. Similarly, nine gallons of the basic regenerant which initially contains 4 weight percent sodium hydroxide can generally be employed to regenerate one gallon of the depleted anion exchanger approximately nine times. Thus, nine volumes of the basic regenerant could be employed to regenerate one volume of the anion exchanger in nine separate cycles in accordance with the methods of this invention.

All of the process steps, including the extraction of biuret from the biuret-containing urea solution and the anion exchanger washing and regeneration steps can be performed either by batch contacting or by the more efficient continuous plug flow contacting in which the urea feed and regenerant solutions are passed through the anion exchanger which is retained in a relatively fixed bed. Plug flow systems can be operated either downflow or upflow, although downflow systems are generally preferred.

Each increment of the biuret-containing urea solution is usually contacted with the anion exchanger for a period of at least about 30 seconds, preferably at least about one minute, most preferably at least about 5 minutes, and generally about one minute to about one hour. Contact times of about 5 to about 30 minutes are usually adequate to effect the desired degree of biuret removal from the urea feed solution. Such contact times correspond to flow rates of about 2 bed volumes per minute or less, preferably about 1 bed volume per minute or less, most preferably about 0.2 bed volumes per minute or less, and usually about 0.02 to about 1 bed volume per minute.

Contact of the anion exchanger with the biuretcontaining feed is usually continued until the desired quantity of low biuret urea solution has been prepared or until the capacity of the anion exchanger is depleted. Depletion of exchanger capacity is indicated in the preferred continuous, fixed bed systems by biuret breakthrough which occurs when a detectable quantity of biuret is present in the urea solution product recovered from the anion exchanger. However, when greater quantities of biuret can be tolerated in the urea product, the biuret extraction step can be continued past the point of biuret breakthrough. The level of biuret acceptable in the urea solution product can be set at any acceptable level, e.g., 60 ppm, 0.5 weight percent, etc.

After completion of the biuret extraction step the urea solution remaining in contact with the anion exchanger can be recovered from the anion exchanger and either returned to the urea feed solution reservoir, to the product accumulator, or otherwise as desired.

It is sometimes desirable, although not essential, to backwash the resin to remove foreign matter, to flush remaining urea solution from the anion exchanger, and/or to "reclassify" the bed of anion exchanger particles. Backwashing is usually effected by passing water rapidly upwardly through the bed to expand the bed by, e.g., 50 percent, after which the anion exchanger is regenerated.

The anion exchanger then can be regenerated by contact under ion exchange conditions with an aqueous regenerant such as an aqueous solution of a strong base or with a substantially non-alkaline aqueous medium, e.g., water or other aqueous media. Both a non-alkaline medium and an aqueous solution of a strong base can be employed sequentially and preferably in that order.

The use of water or other non-alkaline aqueous media as an anion exchanger regenerant, either alone or employed sequentially with the aqueous solution of a strong base, is one of several novel features of the methods of this invention. Regeneration of the anion exchanger with water or other non-alkaline aqueous media is conducted under ion exchange conditions and distinguishes from water washing which usually involves much lower volumes of water which are passed through the anion exchanger at a much more rapid rate than is involved in ion exchange. Indeed, we have found that when a non-alkaline aqueous medium such as water is slowly passed over the anion exchanger containing retained biuret under conditions of contact time and regenerant volume suitable for ion exchange, the non-alkaline aqueous medium removes a substantial proportion of the retained biuret from the anion exchanger.

Regeneration of the anion exchanger is achieved by contacting the anion exchanger with a sufficient quantity of the aqueous regenerant for a period of time sufficient to remove a substantial proportion of the retained biuret from the anion exchanger. The contact time and regenerant volume required to achieve the desired degree of regeneration depends, in part, on the strength of the regenerant, the basicity of the anion exchanger, the quantity of biuret and/or other contaminants which are to be removed from the anion exchanger, and, to a lesser extent, on the method of contacting employed -- batch or continuous. Longer contact times and/or larger regenerant volumes are generally required when using weaker (less basic) regenerants, stronger (more basic) anion exchangers, and/or batch contacting. Surprisingly, however, we have found that water and other non-alkaline aqueous media, although not basic in the usual sense of that term, are very effective for the removal of biuret from even very strong anion exchangers. Indeed, water is as effective for this purpose as dilute ammonium hydroxide (10 weight percent ammonia) and is more effective than concentrated ammonium hydroxide (25 weight ammonia percent). Continuous, plug flow (preferably downflow) regeneration is generally much more efficient than is batch mixing and is therefore preferred.

A substantial proportion of the retained biuret usually can be removed by contacting the anion exchanger with a sufficient quantity of the aqueous regenerant for a period of at least about 20 minutes, preferably at least about 30 minutes, and generally about 30 minutes to about 10 hours. Regenerant volume is conveniently expressed in terms of the volume of anion exchanger to be regenerated (bed volumes in fixed bed systems) and will usually correspond to at least about 5, preferably at least about 8, most preferably at least about 12, and generally about 5 to about 100 volumes of regenerant per volume of anion exchanger. The rate at which the regenerant is passed over the anion exchanger, in the preferred plug flow technique, is conveniently expressed in terms of bed volumes of regenerant per unit time and usually corresponds to about 3 bed volumes per minute or less, preferably about 1 bed volume per minute or less, most preferably about 0.5 bed volumes per minute or less, and generally about 0.05 to about 1 bed volumes per minute.

Batch regeneration is usually accomplished by contacting the biuret-containing anion exchanger with a portion, e.g., 5 to 50 percent of the total regenerant volume to be employed for a period of time sufficient to allow the anion exchanger and regenerant to reach equilibrium. The contact time required for the anion exchanger to reach equilibrium with an increment of regenerant in batch regeneration is usually less than that required when continuous, plug flow regeneration is employed and generally corresponds to about 5 to about 50 percent of the contact time discussed above with respect to continuous regeneration. However, since batch regeneration usually requires a number of contacting steps each of which employ a separate increment of regenerant, the total contact time required for batch regeneration is usually the same as or greater than that required in the preferred plug flow system.

Regeneration is usually continued until the activity of the anion exchanger has been sufficiently restored to allow its efficient reuse for the removal of biuret from additional quantities of the biuret-containing urea feed solution. It is generally desirable to continue regeneration until at least about 80 percent, and preferably at least about 90 percent, of the initial biuret exchange capacity of the anion exchanger has been restored. The extent of regeneration can be conveniently determined by monitoring the biuret content in the regenerant effluent from the anion exchanger during regeneration. Regeneration can be terminated when the biuret content of the effluent has diminished to some acceptable level such as 200 parts per million or less. More complete regeneration is evidenced by lower biuret concentrations in the regenerant effluent After regeneration is complete, the anion exchanger optionally can be washed to remove residual regenerant and can be employed to remove biuret from additional quantities of the urea feed solution.

The several aspects, objects and advantages of the methods of this invention can be better understood by reference to the drawing, which schematically illustrates one embodiment of an anion exchange system useful in the methods of this invention and which includes ion exchange vessel 1, biuret-containing urea feed solution reservoir 7, acidic chloride regenerant reservoir 5, basic regenerant feed reservoir 6, recycle reservoir accumulator 9 and the more essential process flow lines. As illustrated in the drawing, biuret-containing urea feed solution is passed from reservoir 7 via lines 11, 12 and 13 through distributor 4 and into contact with the hydroxide ion form of a basic anion exchanger retained in fixed bed 2. Urea solution of reduced biuret content is removed from vessel 1 via line 14 and 15. Following completion of the biuret extraction step of the cycle, the anion exchanger bed 2 can be backwashed by municipal water which enters the system via line 19 and is passed to the lower portion of vessel 1 via lines 20 and 14. Overflow from the backwashing step exits vessel 1 via line 30 and can be passed to waste. In the alternative, before anion exchanger 2 is backwashed with water, residual urea solution can be washed downwardly through the bed by passing water into the vessel 1 via lines 19, 18, 13 and distributor 4 and can be removed from vessel 1 via lines 14 and 15 and returned to feed storage vessel 7 by conduits not illustrated in the drawing.

In one preferred embodiment of this invention, the anion exchanger washing steps are performed using water which has been treated to reduce its calcium equivalent and/or equivalent carbonate anion content. A system suitable for accomplishing this objective is illustrated schematically by vessel 8 which can be a treated water reservoir or an ion exchange vessel containing an ion exchanger which is capable of reducing the carbonate and/or calcium equivalent content of water entering the vessel via line 16. Treated water is passed from vessel 8 via lines 17, 18 and 13 through distributor 4 to downwash the anion exchanger bed 2 and optionally can be passed upwardly through the anion exchanger via lines 17, 20, and 14. Treated water from vessel 8 can also be directed via line 31 to supply water of reduced calcium equivalent and/or carbonate content to vessels 5, 6 and 7, via lines 33, 34, and 32 respectively for formation of the desired urea feed, acidic chloride, and aqueous base solutions.

After completion of the exchanger washing step, the anion exchanger can be regenerated with an aqueous regenerant which can be an aqueous solution of a strong base, a substantially non-alkaline aqueous medium, or a combination of the substantially non-alkaline medium and the strong base employed sequentially and preferably in that order as described herein. When water is employed as the regenerant, it can comprise either water from a local source (line 19) or treated water from vessel 8, either of which is preferably passed over the anion exchanger downflow via lines 18 and 13 through distributor 4. Spent aqueous regenerant containing biuret removed from the anion exchanger, is recovered from anion exchange vessel 1 via line 14 and can be discharged from the system via line 15.

As an alternative to regeneration with the substantially non-alkaline aqueous medium described immediately above, or as a supplement to such regeneration, the anion exchanger can be regenerated by contact with an aqueous solution of a strong base useful in the methods of this invention which can be passed from reservoir 6 via lines 23, 21, 12 and 13 through distributor 4 into downflow contact with anion exchanger 2. Basic regenerant solution is recovered from anion exchanger 2 via lines 14 and 24 and can be returned to reservoir 6 via lines 25 and 26. This step of the cycle can be continued until the anion exchanger has been contacted with the desired amount of the aqueous solution of a strong base.

In the alternative, the anion exchange column 1 can be charged with a relatively small quantity, e.g., as little as about 1 to about 2 bed volumes of aqueous base solution from reservoir 6, and the aqueous base effluent from the anion exchanger can be recycled directly into contact with the anion exchanger via lines 14, 36, 21, 12 and 13. For instance, if it is desired to regenerate the anion exchanger with 6 bed volumes of the aqueous solution of a strong base, a lesser quantity of the basic solution, e.g., 2 bed volumes, can be charged to anion exchange vessel 1 as described above and recycled three times via lines 36, 21, 12 and 13. By this procedures, 2 bed volumes of the aqueous basic regenerant can be employed to contact the anion exchanger with the equivalent of 6 bed volumes of regenerant during a single regeneration step.

In another embodiment the methods of this invention provide for the elimination of at least a portion of the biuret from the recycled aqueous solution of a strong base. We have discovered that biuret is gradually eliminated from the recycled base solution by hydrolysis by the strong base, and that biuret elimination can be accelerated by heating the recycled base to a temperature of at least about 40° C., generally within the range of about 40° to about 100° C., for at least about 30 minutes. Such heat treatment of the recycled basic regenerant can be conveniently accomplished in the embodiment illustrated in the drawing by passing regenerant from ion exchange vessel 1 via lines 14, 24 and 27 to vessel 9 provided with heating element 35, filter 10 and vent 28. Treated regenerant is returned to vessel 6 via lines 29 and 26.

Optionally, vessel 9 can also be employed to remove carbonate from the recycled basic regenerant. Carbonate removal can be accomplished by mixing a water soluble metal compound with the basic regenerant in vessel 9 which compound reacts with carbonate to form insoluble carbonate as described herein. Contamination of recycled basic regenerant by metal carbonate precipitate can be prevented by suitable filter means 10 in vessel 9.

Although the regeneration procedures discussed above are generally sufficient to maintain acceptable activity of the anion exchanger for a number of cycles, e.g., 5 cycles or more, alkaline earth and/or carbonate contamination of the anion exchanger may gradually accumulate to the point that exchanger activity and/or capacity becomes unacceptably low. The occurrence of low exchange activity and/or capacity is evidenced, in part, by relatively rapid biuret breakthrough into the ion exchanger effluent during the biuret extraction step and indicates the need for more severe regeneration. Such regeneration can be effected by contacting the anion exchanger with a chloride solution which, in the system illustrated in the drawing, is passed from reservoir 5 via lines 22, 21, 12, and 13 through distributor 4 into contact with anion exchanger 2. Contacting of the anion exchanger with the chloride solution should be continued until a substantial proportion, generally at least about 80 percent, and preferably at least about 90 percent of the anion exchanger capacity has been converted to the chloride form. This degree of chloride exchange is generally sufficient to remove a major proportion of accumulated impurities from the anion exchanger, and it can be effectively accomplished by contacting the anion exchanger with the chloride solution for a period of at least about 2 minutes, generally at least about 5 minutes, and preferably about 5 minutes to about 2 hours. These conditions correspond to the use of at least about 1 bed volume, preferably at least about 2 bed volumes, and generally about 3 to about 60 bed volumes of the chloride solution passed downwardly over the anion exchanger at a rate of less than about 3 bed volumes per minute, preferably less than about 1 bed volume per minute, and most preferably less than 0.5 bed volumes per minute in the continuous fixed bed system illustrated in the drawing.

When the anion exchanger contains substantial amounts of carbonate, carbon dioxide will be generated when the anion exchanger is contacted with an acidic solution. Therefore, if the chloride solution is acidic, provision is preferably made for allowing the carbon dioxide to disengage from the anion exchanger and from the solution. This can be achieved by passing the solution over the anion exchanger in increments or by batch contacting the anion exchanger with the solution outside the column.

Regeneration procedures particularly suitable for any particular anion exchanger are usually available from the manufacturer. However, the regeneration conditions discussed immediately above are generally suitable for most basic anion exchangers which are useful in the methods of this invention.

After completion of the chloride exchange step, the anion exchanger can be reconverted to the active hydroxide ion form by washing the anion exchanger to remove residual chloride solution and regenerating it with the aqueous solution of a strong base as described herein.

Numerous variations and modifications of the methods of this invention as illustrated in the drawing will be apparent to one skilled in the art and are intended to be encompassed within the appended claims. For instance, two or more ion exchange vessels 1 can be employed and dan be operated alternately in two or more steps of the ion exchange cycle. For example, one ion exchanger can be employed to remove biuret from the biuret-containing urea feed solution while another ion exchange vessel can be undergoing regeneration. Similarly, the biuret decomposition and carbonate removal functions which can be performed in vessel 9 also can be performed in separate vessels or in the aqueous base regenerant reservoir 6.

The anion exchanger can also be regenerated or otherwise separated from accumulated deposits and/or impurities by removing it from anion exchange vessel 1 and treating the anion exchanger, ex situ of the system, sequentially with chloride solution, concentrated aqueous solution of a strong base, e.g., 25 weight percent sodium hydroxide, or other regeneration medium which may be recommended by the manufacturer or which is known in the art. The regenerated anion exchanger then can be re-packed in the anion exchange vessel for reuse. Indeed, all steps of the process can be conducted by batch processing if desired.

The invention is further described by the following examples which are illustrative of specific modes of practicing the invention and are not intended as limiting the scope of the invention as defined by the appended claims.

EXAMPLE 1

This example demonstrates that the aqueous solution of a strong base can be repeatedly employed to remove biuret from and regenerate basic anion exchangers.

A glass column is packed to a height of 60 cm. with 280 ml. of the chloride form of the anion exchanger marketed by Rohm & Haas Company under the trademark Amberlite IRA-458. The anion exchanger was converted to the active hydroxide form by contact with 4 weight percent aqueous sodium hydroxide solution which is formed from deionized water (free of carbonate ion and calcium equivalents) by passing approximately 10 bed volumes (2.8 liters) of the sodium hydroxide solution downwardly over the anion exchanger bed at a rate of approximately 0.2 bed volumes per minute. The hydroxide exchanged anion exchanger is then washed with deionized water passed downflow over the exchanger to remove residual sodium hydroxide. The sodium hydroxide-containing chloride ion removed from the anion exchanger is discharged from the system.

The thus activated anion exchanger is then employed to remove biuret from an aqueous solution containing 45 weight percent urea and about 1 weight percent biuret which is formed by dissolving biuret-containing urea in deionized water. The urea solution is passed downwardly over the anion exchanger at a rate of about 0.2 bed volumes per minute until biuret breakthrough is observed at which time the anion exchanger has removed 14.3 grams of biuret from the urea solution feed. This corresponds to a biuret capacity of approximately 51 grams biuret per liter of anion exchanger.

The anion exchanger is then drained to remove residual urea solution and is regenerated by contact with 4 weight percent sodium hydroxide solution formed from deionized water which is passed downwardly over the anion exchanger at a rate of approximately 0.2 bed volumes per minute.

After each regeneration cycle the sodium hydroxide regenerant is recovered and returned to the regenerant reservoir which initially contains 10 bed volumes (2.8 liters) of 4 weight percent sodium hydroxide regenerant which is not replenished during the operation.

The biuret extraction and sodium hydroxide regeneration steps are repeated 16 times for a total of 17 cycles. Sodium hydroxide regenerant volume employed in each cycle varies from 5.4 to 21 bed volumes per cycle with the average being about 9 bed volumes per cycle which is sufficient to regain the initial biuret removal capacity of the anion exchanger through 15 cycles of operation. Exchanger capacity for removing biuret from the urea feed solution diminishes in the 16th and 17th cycles indicating the accumulation of impurities on the anion exchanger and substantial reduction of the regenerative ability of the sodium hydroxide regenerant.

After the 17th cycle the anion exchanger is regenerated with approximately 10 bed volumes of fresh 4 weight percent sodium hydroxide solution formed from deionized water which is passed downwardly over the anion exchanger at a rate of about 0.2 bed volumes per minute. This regeneration is sufficient to restore the activity of the anion exchanger for the removal of biuret from the urea feed solution to a level of about 50 grams of biuret per liter of packed anion exchanger bed which corresponds to the initial activity of the anion exchanger.

EXAMPLE 2

This example illustrates that the use of urea feed solutions, regenerant solutions, and process water which have been treated to reduce carbonate and calcium equivalent content, markedly improves anion exchanger activity and useful life for the removal of biuret from biuret-containing aqueous solutions.

The operation described in Example 1 is repeated by passing the biuret-containing aqueous urea solution described in Example 1 downwardly over the anion exchanger employed in Example 1 until biuret breakthrough is observed. The anion exchanger is then drained of urea feed solution, regenerated with 4 weight percent sodium hydroxide solution formed from deionized water, and water-rinsed to remove residual sodium hydroxide solution as described in Example 1 with the exception that the rinse water employed is obtained from the municipal water supply and contains about 300 ppm total dissolved solids and about 150 ppm equivalent calcium carbonate. This calcium content corresponds to about 70 ppm equivalent calcium or 3.5 calcium milliequivalents per liter. This operation is repeated three additional times for a total of four cycles. The municipal water rinse volume is approximately 10.5 bed volumes per cycle and the sodium hydroxide regenerant (10 bed volumes total sodium hydroxide solution) is recovered and reused in each successive cycle.

After the completion of the fourth cycle the activity of the anion exchanger for the removal of biuret from the urea feed solution has been diminished by 50 percent to an equivalent of about 25 grams of biuret per liter of anion exchanger.

EXAMPLE 3

This operation demonstrates that a basic anion exchanger containing retained biuret which has been removed from an aqueous urea solution can be regenerated by contact with water which has been treated to reduce its calcium equivalent content and carbonate content.

The ion exchange column described in Example 1 is charged to a packed volume of 200 ml with the chloride form of Amberlite IRA-458 which is converted to the hydroxide form as described in Example 1. The resulting hydroxide form of the anion exchanger is then employed to remove biuret from an aqueous urea solution containing 45 weight percent urea and 0.44 weight percent biuret which was formed by dissolving urea containing approximately 1 weight percent biuret in deionized water. The urea solution is passed downwardly over the anion exchanger at a rate of about 0.2 bed volumes per minute until biuret is detected in the urea solution effluent from the anion exchanger at a detection limit of 60 ppm biuret. At this point, 2,040 grams of the aqueous urea solution have been passed over the anion exchanger and 9.2 grams of biuret have been retained on the anion exchanger, representing complete recovery of biuret from the urea feed solution.

The anion exchanger is then drained to remove residual urea feed solution and is contacted with 20 bed volumes of deionized water which is passed downwardly over the anion exchanger at a rate of 0.2 bed volumes per minute. This treatment is sufficient to remove 7.0 grams of biuret from the anion exchanger which corresponds to 76 percent biuret recovery.

EXAMPLE 4

The operation described in Example 3 is repeated with the exception that anion exchanger Amberlite IRA-900 is substituted for Amberlite IRA-458. All other conditions are the same as described in Example 3.

Biuret is first detected in the urea solution effluent from the anion exchanger after 2,000 grams of urea solution have been passed over the anion exchanger. This corresponds to a biuret retention of 8.8 grams of biuret on the anion exchanger.

The Amberlite IRA-900 is regenerated by contacting it with 20 bed volumes of deionized water passed downwardly over the resin at a rate of 0.2 bed volumes per minute. This regeneration removes 7.8 grams of biuret from the anion exchanger representing a biuret recovery of 88.3 percent.

EXAMPLE 5

The operation described in Example 3 is repeated with the exception that anion exchanger Amberlite IRA-400 is substituted for Amberlite IRA-458. All other conditions including feedstocks and regenerants are the same as described in Example 3.

Biuret is first detected in the urea solution effluent from the anion exchanger after 2,340 grams of urea feed solution have been passed through the anion exchange column at which time 10.3 grams of biuret have been retained on the anion exchanger. The biuret-containing anion exchanger is regenerated with deionized water as described in Example 3 to recover 7.9 grams of biuret which represents a biuret recovery efficiency of 76.7 percent.

EXAMPLE 6

Amberlite IRA-400 anion exchanger is packed into a tubular glass ion exchange column in the manner described in Example 1 and is converted to the hydroxide form by exchange with 4 weight percent sodium hydroxide solution (formed from deionized water). The anion exchanger is then washed with deionized water to remove residual sodium hydroxide solution as described in Example 1. The packed exchanger bed contains approximately 200 ml. of the exchanger and has a finished bed height of about 35 cm. The anion exchanger is then contacted with aqueous urea solution containing 50 weight percent urea and 0.6 weight percent biuret (1.2 weight percent biuret based on urea) passed downflow through the anion exchange column at a rate of 0.1 bed volumes per minute until biuret is first detected in urea solution effluent from the anion exchange column. The column is then drained to remove residual urea solution and is backwashed with deionized water to physically reclassify the resin beads according to size and to remove particulate matter from the anion exchanger bed.

Biuret is first observed in the urea solution effluent from the anion exchange column after the column has removed the equivalent of 0.57 milliequivalents of biuret per ml. of anion exchanger.

The anion exchanger is then regenerated by contacting with 32.5 bed volumes of deionized water passed downwardly through the anion exchanger column at a flow rate of 0.07 bed volumes per minute.

The regenerated anion exchanger is then employed to remove biuret from additional quantities of the urea feed solution under the conditions employed in the first cycle of this operation. Urea solution flow is continued until biuret is detected in the urea solution effluent from the anion exchange column which occurs after the anion exchanger has removed the equivalent of 0.48 milliequivalents of biuret per ml. of anion exchanger.

The anion exchanger is backwashed and regenerated with deionized water a second time under the conditions employed in the first regeneration step with the exception that 37.5 bed volumes of deionized water regenerant are employed in this step.

The anion exchanger is employed to remove biuret from a third quantity of the urea feed solution until biuret is detected in the urea solution effluent which occurs after the anion exchanger has removed the equivalent of 0.45 milliequivalents of biuret per ml. of resin.

These results demonstrate that regeneration with water which has been treated to reduce its equivalent calcium and/or carbonate content is adequate to enable the repeated use of anion exchangers for the removal of biuret from biuret-containing urea solutions.

Numerous variations and modifications of the concepts of this invention will be apparent to one skilled in art in view of the aforegoing disclosure, the drawing, and the appended claims, and are intended to be encompassed within the scope of this invention defined by the following claims.

We claim:
1. A multi-cycle process for reducing the biuret content of a biuret-containing, aqueous urea solution in which method each cycle comprises the steps of
    (A) contacting a quantity of said biuret-containing urea solution with the hydroxide ion form of an anion exchanger under conditions sufficient to remove at least a portion of said biuret from said quantity of said urea solution and retain the biuret thus removed on said anion exchanger,
    (B) recovering the thus formed urea solution of reduced biuret content from said anion exchanger,
    (C) regenerating said anion exchanger containing said retained biuret by contact with an aqueous regenerant under conditions sufficient to remove at least a portion of said biuret from said anion exchanger, and
    (D) recovering the thus formed biuret-containing regenerant from said anion exchanger,
wherein, in at least one cycle, said aqueous regenerant comprises an aqueous solution of a strong base which previously has been employed to regenerate a biuret-containing anion exchanger other than in said one cycle.

2. The method defined in claim 1 wherein said aqueous solution of a strong base recovered from said anion exchanger is employed to regenerate a biuret-containing anion exchanger for a total of at least two cycles.

3. The method defined in claim 2 wherein said aqueous solution of a strong base has been recovered from said anion exchanger in a preceding cycle and is employed for said regeneration of said biuret-containing anion exchanger for a total of at least about four cycles.

4. The method defined in claim 1 wherein said anion exchanger is retained in a fixed bed and is contacted with at least about 5 bed volumes of said regenerant over a period of at least about 20 minutes in said regenerating step.

5. The method defined in claim 1 wherein said aqueous solution of a strong base comprises at least about 0.5 weight percent of a member selected from the group consisting of sodium hydroxide, potassium hydroxide, and combinations thereof.

6. The method defined in claim 1 wherein said aqueous solution of a strong base comprises about 0.5 to about 15 weight percent of a member selected from the group consisting of sodium hydroxide, potassium hydroxide, and combinations thereof.

7. The method defined in claim 1 which further comprises the step of heating said aqueous solution of a strong base to a temperature of at least about 40° C. after it has been recovered from said anion exchanger in said regenerating step of at least one cycle.

8. The method defined in claim 1 which further comprises the step of removing carbonate from said aqueous solution of a strong base.

9. The method defined in claim 7 which further comprises the step of removing carbonate from said aqueous urea solution of a strong base.

10. The method defined in claim 1 which further comprises the step of mixing with said aqueous solution of a strong base an alkaline earth metal compound which reacts with carbonate contained in said aqueous solution of a strong base to form the corresponding insoluble alkaline earth metal carbonate and precipitating the resulting alkaline earth metal carbonate from said aqueous solution of said strong base.

11. The method defined in claim 10 wherein said alkaline earth metal is selected from the group consisting of calcium, magnesium, and combinations thereof.

12. The method defined in claim 7 which further comprises the step of mixing with said aqueous solution of said strong base a water-soluble alkaline earth metal compound which reacts with carbonate to form the corresponding insoluble alkaline earth metal carbonate and precipitating the thus formed alkaline earth metal carbonate from said aqueous solution of said strong base.

13. The method defined in claim 12 wherein said alkaline earth metal comprises a member selected from the group consisting of calcium, magnesium, and combinations thereof.

14. The method defined in claim 1 wherein said anion exchanger containing said retained biuret is contacted, in at least of one of said cycles, with at least about 5 volumes of a substantially non-alkaline aqueous regenerant per volume of said anion exchanger for a period of at least about 20 minutes sufficient to remove at least a portion of said retained biuret from said anion exchanger.

15. The method defined in claim 1 wherein, in at least one cycle, said anion exchanger containing said retained biuret is contacted with at least about 8 volumes of a substantially non-alkaline aqueous regenerant per volume of said anion exchanger for a period of at least about 30 minutes sufficient to remove at least a portion of said retained biuret from said anion exchanger, and the resulting anion exchanger having a reduced retained biuret content is contacted with said aqueous solution of a strong base before it is contacted with an additional quantity of said biuret-containing urea solution.

16. The method defined in claim 14 wherein said anion exchanger is contacted with said substantially non-alkaline aqueous regenerant for at least about 30 minutes.

17. The method defined in claim 14 wherein said anion exchanger is retained in a fixed bed having a bed volume corresponding to the bulk volume of said anion exchanger in said fixed bed, and said anion exchanger is contacted with at least about 12 bed volumes of said substantially non-alkaline aqueous regenerant at a flow rate of about 3 bed volumes per minute or less.

18. The method defined in claim 1 wherein said anion exchanger containing said retained biuret is contacted, in each cycle, with at least about 8 volumes of a substantially non-alkaline aqueous regenerant per volume of said anion exchanger for a period of at least about 30 minutes and is then contacted with said aqueous solution of said strong base.

19. The method defined in claim 1 wherein, in at least one cycle, said aqueous regenerant is substantially free of said strong base.

20. The method defined in claim 1 wherein, in at least one cycle, said aqueous regenerant consists essentially of one or more aqueous solutions containing less than 0.1 weight percent of a strong base.

21. The method defined in claim 20 wherein said aqueous regenerant contains less than about 1 calcium milliequivalent per liter.

22. The method defined in claim 1 wherein at least one of said biuret-containing urea solution and said aqueous regenerant contain less than about 0.5 calcium milliequivalents per liter.

23. The method defined in claim 1 wherein at least one of said biuret-containing urea solution and said aqueous regenerant contain less than about 0.2 calcium milliequivalents per liter.

24. The method defined in claim 1 wherein said biuret-containing urea solution and said aqueous regenerant contain less than about 0.5 calcium milliequivalents per liter.

25. The method defined in claim 1 wherein at least one of said biuret-containing urea solution and said aqueous regenerant are prepared from water which contains less than about 1 calcium milliequivalent per liter.

26. The method defined in claim 25 wherein said water contains less than about 0.2 calcium milliequivalents per liter.

27. The method defined in claim 1 wherein said biuret-containing urea solution and said aqueous regenerant are prepared from water which contains less than about 0.2 calcium milliequivalents per liter.

28. The method defined in claim 1 wherein at least one of said biuret-containing urea solution and said aqueous regenerant has been treated to reduce its calcium equivalent content.

29. The method defined in claim 1 wherein said biuret-containing urea solution and said aqueous regenerant have been treated to reduce their calcium equivalent content.

30. The method defined in claim 1 wherein at least one of said biuret-containing urea solution and said aqueous regenerant comprises water which has been treated to reduce its calcium equivalent content.

31. The method defined in claim 30 wherein said water is selected from the group consisting of deionized water, distilled water, sodium-exchanged water, hydrogen exchanged water, and combinations thereof.

32. The method defined in claim 1 wherein said biuret-containing urea solution and said aqueous regenerant comprise water which has been treated to reduce its calcium equivalent content.

33. The method defined in claim 32 wherein said water is selected from the group consisting of deionized water, distilled water, sodium-exchanged water, hydrogen exchanged water, and combinations thereof.

34. The method defined in claim 32 wherein said water has been prepared by removing at least a portion of the alkaline earth metals from a water source containing alkaline earth metals.

35. The method defined in claim 1 wherein said anion exchanger is retained in a fixed bed having a bed volume corresponding to bulk volume of said anion exchanger, and said biuret-containing aqueous urea solution is passed through said fixed bed at a rate corresponding to about 2 bed volumes per minute or less until the aqueous urea solution exiting said fixed bed contains at least a detectable quantity of biuret.

36. The method defined in claim 1 wherein said anion exchanger is retained in a fixed bed, and said anion exchanger containing said biuret is contacted during at least one of said cycles with a biuret-containing, aqueous solution of a strong base recovered from said anion exchanger in a previous cycle.

37. The method defined in claim 1 wherein, in at least one cycle, said aqueous solution of a strong base has been recovered from said anion exchanger in a previous cycle.

38. The method defined in claim 1 wherein said anion exchanger is retained in a fixed bed having a bed volume corresponding to the bulk volume of said anion exchanger during said contacting and regenerating steps, in at least one cycle, said biuret-containing anion exchanger is regenerated by contact with a total volume of said aqueous solution of a strong base corresponding to at least about 5 bed volumes, and at least a portion of said aqueous solution of a strong base with which said biuret-containing anion exchanger is contacted in at least said one cycle has been recovered from and recycled into contact with said biuret-containing anion exchanger in the same cycle.

39. The method defined in claim 1 which further comprises the steps of periodically exchanging at least a portion of the ion exchange capacity of said anion exchanger to the chloride ion form and reexchanging said exchange capacity with strong base to the hydroxide ion form.

40. The method defined in claim 41 wherein at least about 90 percent of said ion exchange capacity is exchanged to said chloride ion form and is reexchanged to said hydroxide ion form.

41. A multi-cycle process for reducing the biuret content of a biuret-containing, aqueous urea solution in which method each cycle comprises the steps of
  (A) contacting a quantity of said biuret-containing urea solution with the hydroxide ion form of an anion exchanger under conditions sufficient to remove at least a portion of said biuret from said quantity of said urea solution and retain the biuret thus removed on said anion exchanger,
  (B) recovering the thus formed urea solution of reduced biuret content from said anion exchanger,
  (C) regenerating said anion exchanger containing said retained biuret by contact with an aqueous regenerant under conditions sufficient to remove at least a portion of said biuret from said anion exchanger, and
  (D) recovering the thus formed biuret-containing regenerant from said anion exchanger,
wherein, in at least one cycle, said aqueous regenerant comprises an aqueous solution of a strong base which has been employed to regenerate a biuret-containing anion exchanger in at least three previous cycles.

42. A multi-cycle process for reducing the biuret content of a biuret-containing, aqueous urea solution in which method each cycle comprises the steps of
  (A) contacting a quantity of said biuret-containing urea solution with the hydroxide ion form of an anion exchanger under conditions sufficient to remove at least a portion of said biuret from said quantity of said urea solution and retain the biuret thus removed on said anion exchanger,
  (B) recovering the thus formed urea solution of reduced biuret content from said anion exchanger,
  (C) regenerating said anion exchanger containing said retained biuret by contact with an aqueous regenerant under conditions sufficient to remove at least a portion of said biuret from said anion exchanger, and
  (D) recovering the thus formed biuret-containing regenerant from said anion exchanger,
wherein, in at least one cycle, said aqueous regenerant comprises an aqueous solution of a strong base which previously has been employed to regenerate a biuret-containing anion exchanger, and at least one of said biuret-containing urea solution and said aqueous regenerant comprise water which has been treated to reduce its calcium equivalent content.

43. A multi-cycle process for reducing the biuret content of a biuret-containing, aqueous urea solution in which method each cycle comprises the steps of
  (A) contacting a quantity of said biuret-containing urea solution with the hydroxide ion form of an anion exchanger under conditions sufficient to remove at least a portion of said biuret from said quantity of said urea solution and retain the biuret thus removed on said anion exchanger,
  (B) recovering the thus formed urea solution of reduced biuret content from said anion exchanger,
  (C) regenerating said anion exchanger containing said retained biuret by contact with an aqueous regenerant under conditions sufficient to remove at least a portion of said biuret from said anion exchanger, and
  (D) recovering the thus formed biuret-containing regenerant from said anion exchanger,
wherein, in at least one cycle, said aqueous regenerant comprises an aqueous solution of a strong base which previously has been employed to regenerate a biuret-containing anion exchanger, and said biuret-containing urea solution and said aqueous regenerant comprise water which has been treated to reduce its calcium equivalent content.

44. A multi-cycle process for reducing the biuret content of a biuret-containing, aqueous urea solution in which method each cycle comprises the steps of
  (A) contacting a quantity of said biuret-containing urea solution with the hydroxide ion form of an anion exchanger under conditions sufficient to remove at least a portion of said biuret from said quantity of said urea solution and retain the biuret thus removed on said anion exchanger,
  (B) recovering the thus formed urea solution of reduced biuret content from said anion exchanger,
  (C) regenerating said anion exchanger containing said retained biuret by contact with an aqueous regenerant under conditions sufficient to remove at least a portion of said biuret from said anion exchanger, and
  (D) recovering the thus formed biuret-containing regenerant from said anion exchanger,
wherein, in at least one cycle, said aqueous regenerant comprises an aqueous solution of a strong base which comprises at least about 2 weight percent of a member selected from the group consisting of sodium hydroxide, potassium hydroxide, and combinations thereof, which previously has been employed to regenerate a biuret-containing anion exchanger, and said anion exchanger is contacted with at least about 5 bed volumes of a substantially non-alkaline aqueous regenerant for a period of at least about 20 minutes sufficient to remove at least a portion of said retained biuret from said anion exchanger before said anion exchanger is contacted with said aqueous solution of a strong base.

45. The method defined in claim 44 wherein, in each cycle, said anion exchanger containing said retained biuret is contacted with said substantially non-alkaline aqueous regenerant and is then contacted with said aqueous solution of a strong base, and said biuret-containing urea solution, said aqueous solution of a strong base, and said substantially non-alkaline aqueous regenerant comprise water which has been treated to reduce its calcium equivalent content.

46. A multi-cycle process for reducing the biuret content of a biuret-containing, aqueous urea solution in which method each cycle comprises the steps of (A) contacting a quantity of said biuret-containing urea solution with the hydroxide ion form of an anion exchanger under conditions sufficient to remove at least a portion of said biuret from said quantity of said urea solution and retain the biuret thus removed on said anion exchanger, (B) recovering the thus formed urea solution of reduced biuret content from said anion exchanger, (C) regenerating said anion exchanger containing said retained biuret by contact with an aqueous regenerant under conditions sufficient to remove at least a portion of said biuret from said anion exchanger, and (D) recovering the thus formed biuret-containing regenerant from said anion exchanger, wherein, in at least one cycle, said aqueous regenerant comprises an aqueous solution of a strong base comprising at least about 0.5 weight percent of a member selected from the group consisting of sodium hydroxide, potassium hydroxide, and combinations thereof, which previously has been employed to regenerate a biuret-containing anion exchanger, and wherein, in at least one other cycle, said aqueous regenerant consists essentially of one or more substantially non-alkaline aqueous media which contain less than about 0.1 weight percent of a strong base.

47. A method for regenerating a biuret-containing basic anion exchanger which method comprises the step of contacting said biuret-contaning anion exchanger in at least one cycle of a multicycle process with an aqueus solution of a strong base which previously has been employed to regenerate a biuret-containing anion exchanger other than in said one cycle.

* * * * *